(12) United States Patent
Sun et al.

(10) Patent No.: US 8,384,893 B2
(45) Date of Patent: Feb. 26, 2013

(54) RAMAN DETECTING SYSTEM AND DETECTION METHOD FOR USING THE SAME

(75) Inventors: Ying-Hui Sun, Beijing (CN); Xiao-Feng Feng, Beijing (CN); Jiao Miao, Beijing (CN); Xu Xie, Beijing (CN); Kai-Li Jiang, Beijing (CN); Kai Liu, Beijing (CN); Shou-Shan Fan, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 367 days.

(21) Appl. No.: 12/815,545

(22) Filed: Jun. 15, 2010

(65) Prior Publication Data

US 2011/0063612 A1    Mar. 17, 2011

(30) Foreign Application Priority Data

Sep. 15, 2009    (CN) .......................... 2009 1 0190212

(51) Int. Cl.
  *G01J 3/44*    (2006.01)
(52) U.S. Cl. ....................................................... 356/301
(58) Field of Classification Search .................... 356/301
  See application file for complete search history.

(56) References Cited

U.S. PATENT DOCUMENTS

| | | |
|---|---|---|
| 5,818,047 A | 10/1998 | Chaney et al. |
| 2007/0153269 A1 | 7/2007 | Wang et al. |
| 2008/0248235 A1 | 10/2008 | Feng et al. |
| 2009/0224435 A1 | 9/2009 | Gogotsi et al. |
| 2010/0062226 A1 | 3/2010 | Hulteen et al. |
| 2010/0233472 A1 | 9/2010 | Liu et al. |

FOREIGN PATENT DOCUMENTS

| | | |
|---|---|---|
| CN | 1957245 | 5/2007 |
| CN | 101239712 | 8/2008 |
| CN | 101284662 | 10/2008 |
| CN | 101294904 | 10/2008 |
| CN | 101493457 | 7/2009 |
| JP | 2009501904 | 1/2009 |
| JP | 2009184907 | 8/2009 |
| WO | WO2005114298 | 12/2005 |

OTHER PUBLICATIONS

Sanles-Sobrido et al., "Label-free SERS detection of relevant bioanalytes on silver-coated carbon nanotubes: The case of cocaine", 2009, The Royal Society of Chemistry Nanoscales, vol. 1, pp. 153-158.*

Sun et al., "Highly Sensitive Surface-Enhanced Raman Scattering Substrate Made from Superaligned Carbon Nanotubes", Apr. 13, 2010, ACS Nano Letters, 10, pp. 1747-1753.*

(Continued)

*Primary Examiner* — Kara E Geisel

(74) *Attorney, Agent, or Firm* — Altis Law Group, Inc.

(57) ABSTRACT

A Raman detecting system for detecting a vapor of an explosive includes a surface-enhanced Raman scattering substrate for absorbing the vapor of the explosive. The substrate includes a carbon nanotube film structure and a plurality of metallic particles disposed on the carbon nanotube film structure. The carbon nanotube film structure includes a plurality of stacked carbon nanotube films.

19 Claims, 10 Drawing Sheets

OTHER PUBLICATIONS

Chen Yi-Chieh et al, Single-Walled Carbon Nanotube Networks Decorated with Silver Nanoparticles: A Novel Graded SERS Substrate, J.Phys.Chem.C 2007, vol. 111, No. 44, pp. 16167-16173.

Tsai et al. "Electrochemical deposition of silver nanoparticles in multiwalled carbon nanotube-alumina-coated silica for surface-enhanced Raman scattering-active substrates", Electrochemistry Communications, 2009, 11, pp. 542-545.

Zhang et al. Superaligned carbon nanotube grid for high resolution transmission electron microscopy of nanomaterials, Nano Letters, 2008, 8(8), pp. 2564-2569.

* cited by examiner

US 8,384,893 B2

RAMAN DETECTING SYSTEM AND DETECTION METHOD FOR USING THE SAME

CROSS-REFERENCE

This application claims all benefits accruing under 35 U.S.C. §119 from China Patent Application No. 200910190212.X, filed on Sep. 15, 2009 in the China Intellectual Property Office, the disclosure of which is incorporated herein by reference. This application is related to copending applications entitled, "SURFACE-ENHANCE RAMAN SCATTERTING SUBSTRATE AND RAMAN DETECTING SYSTEM HAVING THE SAME", filed on Jun. 15, 2010, and application Ser. No. 12/815,551.

BACKGROUND

1. Technical Field

The present disclosure generally relates to a Raman detecting system for detecting an explosive and a detection method using the Raman detecting system.

2. Description of Related Art

SERS (surface-enhanced Raman scattering) as a potential tool for trance analysis of explosive such as a trinitrotoluene (TNT) has been explored actively due to its sensitivity and reliable identification of molecular structure. A Raman detecting system having a SERS substrate can be provided to detecting the explosive. When the Raman detecting system is in operation, a solid or liquid sample containing the explosive therein can adhere to the SERS substrate directly.

However, samples containing explosives therein can hardly be obtained in some ambient environments, such as in an airport or in a railway station. Thus, detection and identification of explosives existing in some ambient environments is a problem of great practical interest.

What is needed therefore, is a Raman detecting system capable of detecting the explosive and a detecting method for detecting the explosive.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILS DESCRIPTION

Figure 1:
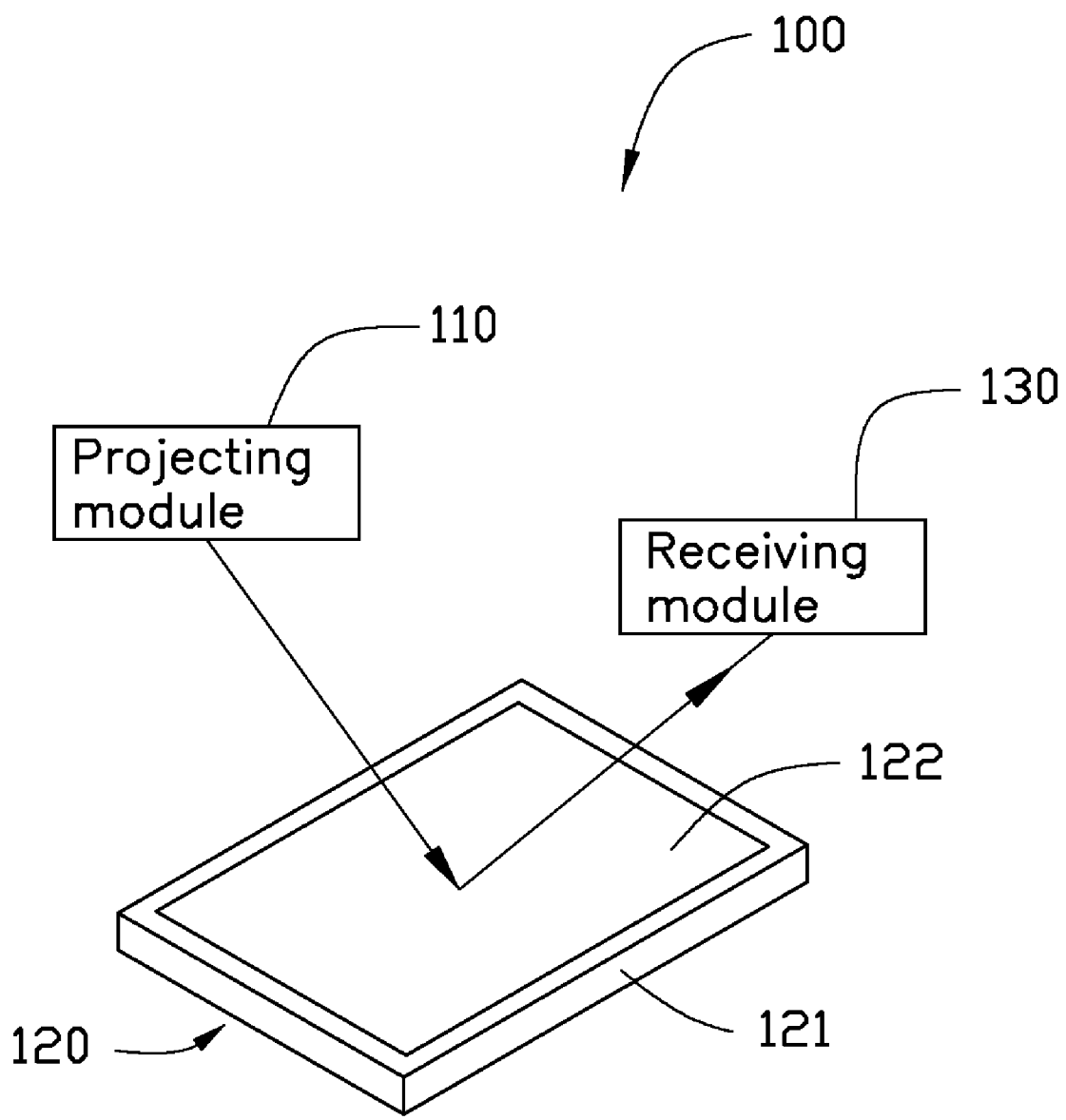
FIG. 1 is a schematic structural view of one embodiment of a Raman detecting system.

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views Referring to FIG. 1, an embodiment of a Raman detecting system 100 includes a projecting module 110, a surface-enhanced Raman scattering (SERS) substrate 120, and a receiving module 130.

The projecting module 110 is configured to project a beam of light to the SERS substrate 120 to form a scattering light. Acreage of a cross section of the beam of light on the SERS substrate 120 can be less than or equal to 2 square millimeters. The projecting module 110 can include a light source such as argon laser. The light source can have a narrower frequency width. The beam of light can have a wavelength of about 450.0 nanometers to about 514.5 nanometers. In one embodiment, the wavelength of the beam of light is about 514.5 nanometers. More scattering light can be obtained by the beam of light with the wavelength of about 514.5 nanometers.

The receiving module 130 is configured to collect the scattering light scattered by the SERS substrate 120 to form a Raman spectra figure of an explosive absorbed on the SERS substrate 120. The receiving module 130 can include a multi-channel photon detector such as charge coupled device (CCD), or a single-channel photon detector such as a photon multiplier. Details of vibration modes of the explosive can be read from the Raman spectra figure formed by the receiving module 130.

The explosive can be a solid explosive, a liquid explosive, or a gas explosive. The explosive can be a trinitrotoluene (TNT), a cyclotetramethylenetetranitramine (HMX), three methyl 3-nitro-amine (RDX), a nitro-amine, a picric acid, a pentaerythritol tetranitrate (PETN), a nitroglycerin, a dinitrotoluene (DNT), an ethylene glycol dinitrate, a triacetone triperoxide, or a TATP.

If the explosive is located in normal atmosphere, some explosives can volatilize in normal atmosphere to form an explosive vapor. A partial gas pressure of the explosive vapor can be defined as vapor pressure. Generally, the vapor pressure of the explosive can be about $1*10^{-4}$ Pa at 25° C. to about 1 Pa at 25° C. In one embodiment, the explosive is TNT, and the vapor pressure of the TNT is about $5*10^{-4}$ Pa at 25° C. Simultaneously, a content of vapor modules of the explosive in normal atmosphere at 25° C. can be about $1*10^{-10}$ to about 1. The content of the vapor modules of the TNT in normal atmosphere at 25° C. can be about $7.7*10^{-9}$.

The SERS substrate 120 is configured to absorb the explosive vapor. When the SERS substrate 120 is irradiated by the beam of light, a part of the beam of light can strike the explosive to form the scattering light. Specifically, some photons of the beam of light can strike the explosive and collide with molecules of the explosive vapor, thus, the momentum or the frequency of the photons can change. The variation of the frequency of the photons can correspond to variation frequencies of chemical bonds in the molecules of the explosive vapor. Thus, the molecular structure can be read from the scattering light.

The SERS substrate 120 can include a supporting element 121 and a carbon nanotube composite film 122.

The supporting element 121 is configured to support or fix the carbon nanotube composite film 122. The supporting element 121 can be a transparent substrate such as a glass panel, a plastic substrate, or a framing element such as a grid framework. Thus, less beams of light can be reflected by the substrate to disturb the scattering light. If the supporting element 121 is a transparent substrate, the carbon nanotube composite film 122 can be disposed on a surface of the transparent substrate directly. If the supporting element 121 is a framing element, the carbon nanotube composite film 122 can be suspended on the framing element. The area of the suspended part of the carbon nanotube composite film 122 can be greater than the cross-sectional area of the beam of light on the SERS substrate 120.

The carbon nanotube composite film 122 can include a carbon nanotube film structure and a metallic film disposed on the carbon nanotube film structure. The carbon nanotube film structure is capable of forming a free-standing structure. The term "free-standing structure" can be defined as a structure that does not have to be supported by a substrate. For example, a free-standing structure can sustain the weight of itself when it is hoisted by a portion thereof without any significant damage to its structural integrity. The free-standing structure of the carbon nanotube film structure is realized by the carbon nanotubes joined by van der Waals attractive force. So, if the carbon nanotube film structure is placed between two separate supporters, a portion of the carbon nanotube film structure, not in contact with the two supporters, would be suspended between the two supporters and yet maintain film structural integrity. Simultaneously, the supporting element 121 is an optional structure and can be omitted, because the carbon nanotube film structure is a free-standing structure.

The carbon nanotube film structure includes a plurality of carbon nanotubes uniformly distributed therein, and joined by van der Waals attractive force therebetween. The carbon nanotubes in the carbon nanotube film structure can be orderly or disorderly arranged. The term 'disordered carbon nanotube film structure' includes, but is not limited to, a structure where the carbon nanotubes are arranged along many different directions, such that the number of carbon nanotubes arranged along each different direction can be almost the same (e.g. uniformly disordered), and/or entangled with each other. 'Ordered carbon nanotube film structure' includes, but is not limited to, a structure where the carbon nanotubes are arranged in a consistently systematic manner, e.g., the carbon nanotubes are arranged approximately along a same direction and or have two or more sections within each of which the carbon nanotubes are arranged approximately along a same direction (different sections can have different directions). The carbon nanotubes in the carbon nanotube film structure can be single-walled, double-walled, and/or multi-walled carbon nanotubes.

Macroscopically, the carbon nanotube film structure may have a substantially planar structure. The planar carbon nanotube structure can have a thickness of about 0.5 nanometers to about 100 microns. The carbon nanotube film structure includes a plurality of carbon nanotubes and defines a plurality of micropores having a size of about 1 nanometer to about 500 nanometers. The carbon nanotube film structure includes at least one carbon nanotube film, the at least one carbon nanotube film includes a plurality of carbon nanotubes substantially parallel to a surface of the corresponding carbon nanotube film.

Figure 2:
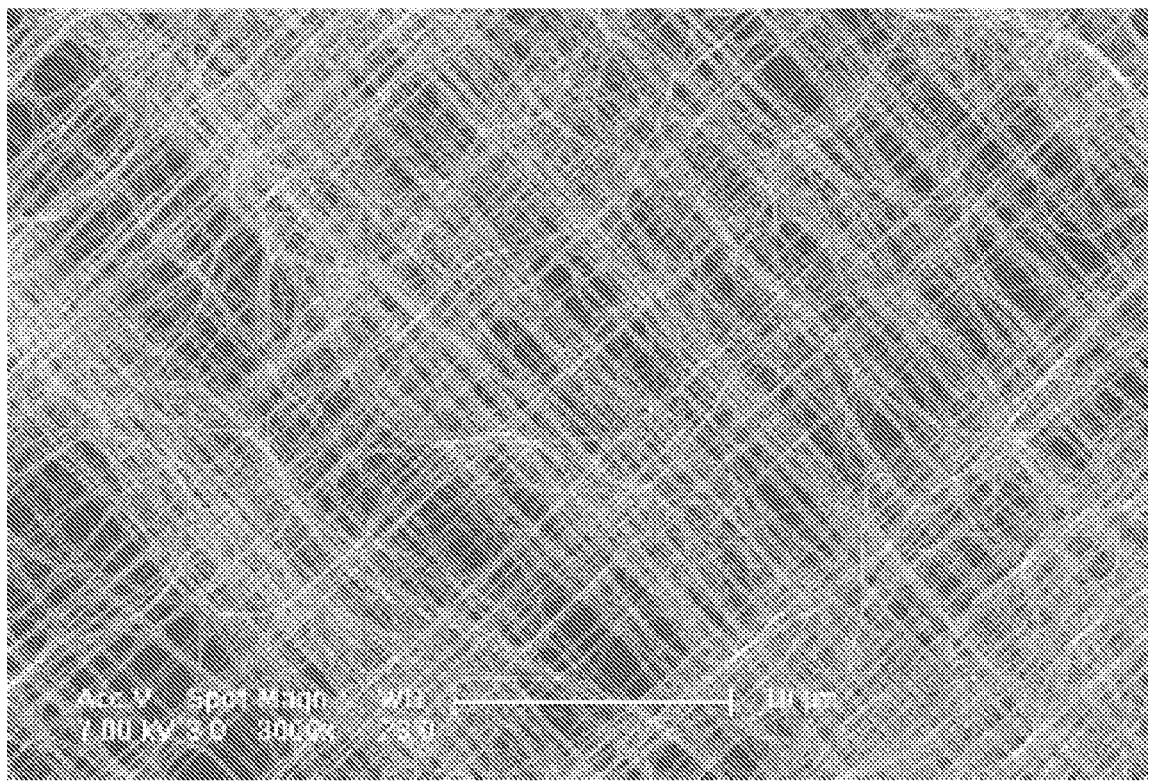
FIG. 2 shows a Scanning Electron Microscope (SEM) image of a carbon nanotube film structure consisting of a plurality of stacked drawn carbon nanotube films defined as a CNT grid.

The carbon nanotube film structure includes a plurality of stacked carbon nanotube films as shown in FIG. 2. The number of the layers of the carbon nanotube films is not limited, provided the thickness of the carbon nanotube film structure can be maintained in a range from about 0.5 nanometers to about 100 microns. In one embodiment, the carbon nanotube film structure includes less than or equal to 10 layers of carbon nanotube films. Adjacent carbon nanotube films can be adhered by only the van der Waals attractive force therebetween.

Figure 3:
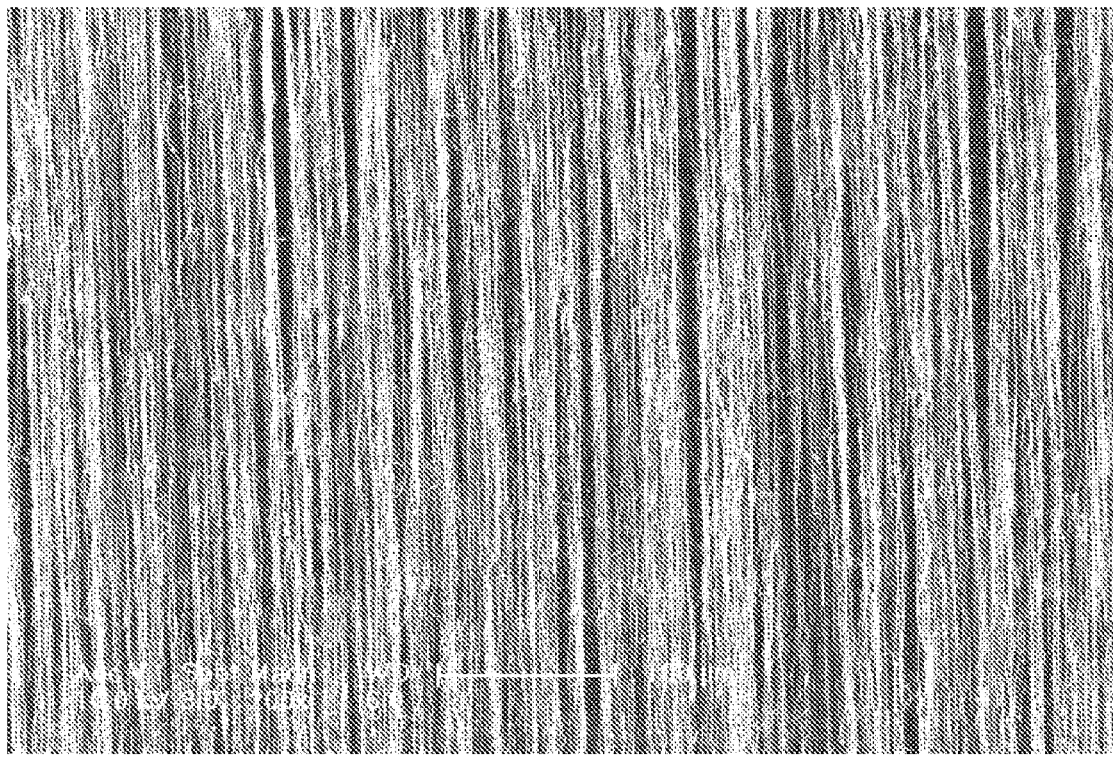
FIG. 3 shows an SEM image of a drawn carbon nanotube film.

Each of the carbon nanotube films can have a thickness of about 0.5 nanometers to about 100 microns. The carbon nanotube film includes a plurality of carbon nanotubes that can be arranged substantially parallel to a surface of the carbon nanotube film as shown in FIG. 3. A plurality of micropores having a size of about 1 nanometer to about 500 nanometers can be defined by the carbon nanotubes. A large number of the carbon nanotubes in the carbon nanotube film can be oriented along a preferred orientation, meaning that a large number of the carbon nanotubes in the carbon nanotube film are arranged substantially along the same direction. An end of one carbon nanotube is joined to another end of an adjacent carbon nanotube arranged substantially along the same direction, by van der Waals attractive force. More specifically, the carbon nanotube film includes a plurality of successively oriented carbon nanotube segments joined end-to-end by van der Waals attractive force therebetween. Each carbon nanotube segment includes a plurality of carbon nanotubes substantially parallel to each other, and joined by van der Waals attractive force therebetween. The carbon nanotube segments can vary in width, thickness, uniformity and shape. A small number of the carbon nanotubes are randomly arranged in the carbon nanotube film, and has a small but not negligible effect on the larger number of the carbon nanotubes in the carbon nanotube film arranged substantially along the same direction. The carbon nanotube film is capable of forming a free-standing structure. The term "free-standing structure" can be defined as a structure that does not have to be supported by a substrate. For example, a free-standing structure can sustain the weight of itself when it is hoisted by a portion thereof without any significant damage to its structural integrity. The free-standing structure of the carbon nanotube film is realized by the successive segments joined end to end by van der Waals attractive force.

Understandably, some variation can occur in the orientation of the carbon nanotubes in the carbon nanotube film as can be seen in FIG. 3. Microscopically, the carbon nanotubes oriented substantially along the same direction may not be perfectly aligned in a straight line, and some curve portions may exist. Furthermore, it can be understood that some carbon nanotubes are located substantially side by side and oriented along the same direction and in contact with each other.

An angle can exist between the carbon nanotubes in adjacent carbon nanotube films. The angle between the aligned directions of the adjacent carbon nanotube films can be about 90 degrees, thus a plurality of substantially uniform micropores can be defined by the carbon nanotube film structure. Simultaneously, aligned directions of adjacent carbon nanotube films are substantially perpendicular to each other, thus a plurality of nodes can be defined by the carbon nanotube film structure. The carbon nanotube film structure including a plurality of uniform micropores and nodes forming a nanoporous structure. The nanoporous structure can provide a huge surface area to adsorb more explosive vapor or explosive molecules therein.

The metallic film can be disposed on one surface of the carbon nanotube film structure or on two opposite surfaces of the carbon nanotube film structure. The metallic film can be formed by means of depositing a metallic material on the carbon nanotube film structure by, for example, e-beam evaporation or sputtering. A quartz crystal oscillator can be used to monitor the film thickness. A material of the metallic film can be noble metal or transition metal. The material of the metallic film can be gold, silver, copper, or nickel. The metallic film can have a thickness of about 1 nanometer to about 50 nanometers. In one embodiment, the metallic film has a thickness of about 18 nanometers to about 22 nanometers. In another embodiment, the metallic film with a thickness of about 3 nanometers to about 7 nanometers can improve the Raman enhancement factor of the SERS substrate 120. Microscopically, the metallic film can include a plurality of metallic particles. The metallic particles can be disposed on the outer surface of the carbon nanotubes of the carbon nanotube film structure. Simultaneously, more metallic particles can be disposed on the carbon nanotubes exposing out of the carbon nanotube film structure. The metallic particles each can have a diameter of about 1 nanometer to about 50 nanometers. A plurality of interparticle gaps can be formed among the metallic particles. The interparticle gap is about 1 nanometer to about 15 nanometers. In other words, gap or space between the metallic particles can be about 1 nanometer to about 15 nanometers. In one embodiment, the interparticle gap is about 2 nanometers to about 5 nanometers. Understandably, less than 1 percent of the metallic particles can have a diameter of about 50 nanometers. Less than 1 percent of the interparticle gap can be greater than 15 nanometers.

The carbon nanotubes of the SERS substrate 120 can define a plurality of uniform micropores and nodes. Thus, the nanoporous structure can adsorb more explosive vapor therein. The Raman detecting system 100 can catch explosive molecules of the explosive without directly contacting a solid or a liquid sample containing the explosive. The metallic particles having a small size can be formed on the carbon nanotube film structure to define a plurality of interparticle gaps with a small size. The smaller the size of the interparticle gap, the greater the electromagnetic enhancement and Raman enhancement factor of the SERS substrate 120. Thus, the Raman detecting system 100 can detect the explosive vapor absorbed in the SERS substrate 120 and explosives.

The composite carbon nanotube film 122 can also/further include a transition layer inserted between the carbon nanotube film structure and the metallic film. The transition layer can be deposited on the carbon nanotube film structure before the evaporation or sputtering of the metallic film. The transition layer can have a thickness of about 10 nanometers to about 100 nanometers. In one embodiment, the transition layer has a thickness of about 15 nanometers to about 30 nanometers. Microscopically, the transition layer can cover part or all the outer surfaces of the carbon nanotubes of the carbon nanotube film structure. The transition layer can provide a surface smoother than the surface of the carbon nanotube film structure. Stresses endured by the metallic particles in all orientations can be substantially equal to each other. Thus, the transition layer can improve the shape regularity of the metallic particles. The metallic particles can tend to form quasi-uniform spheres on the transition layer and improve electromagnetic enhancement and Raman enhancement factor of the SERS substrate 120. A material of the transition layer can be inorganic oxide such as silicon dioxide and magnesium oxide. In one embodiment, the transition layer is a silicon dioxide layer with a thickness of about 20 nanometers.

Figure 4:
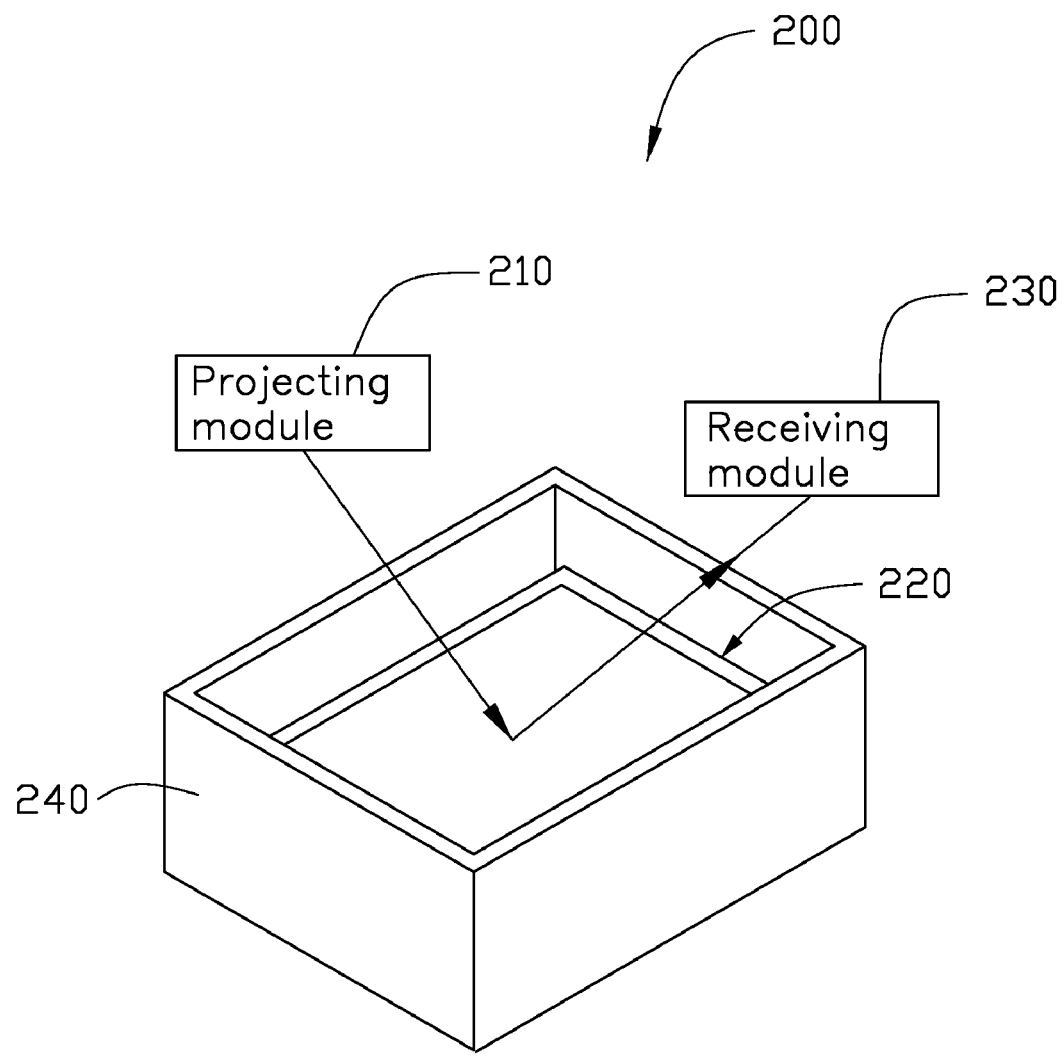
FIG. 4 is a schematic structural view of one embodiment of a Raman detecting system.

Referring to FIG. 4, an embodiment of a Raman detecting system 200 includes a projecting module 210, an SERS substrate 220, a receiving module 230, and a chamber 240. The projecting module 210 can be configured to project a beam of light to the SERS substrate 220 to form a scattering light. The SERS substrate 220 is configured to load the sample. The receiving module 230 is configured to collect the scattering light scattered by the SERS substrate 230 to form a Raman spectra figure. The chamber 240 is configured to receive the sample.

The compositions, features and functions of the Raman detecting system 200 in the embodiment shown in FIG. 4 are similar to the Raman detecting system 100 in the embodiment shown in FIG. 1. The difference is that the Raman detecting system 200 further includes the chamber 240.

The chamber 240 can represent, for example, a room, an airport, a container, a railway station, or a carriage. In one embodiment, the chamber 240 is a sealed chamber such as a desiccator. The explosive vapor can diffuse in the sealed chamber for a longer time. Thus, the vapor pressure of the explosive vapor can keep stable. The SERS substrate 230 can be moved in or fixed on the chamber 240 to absorb the explosive vapor.

Figure 5:
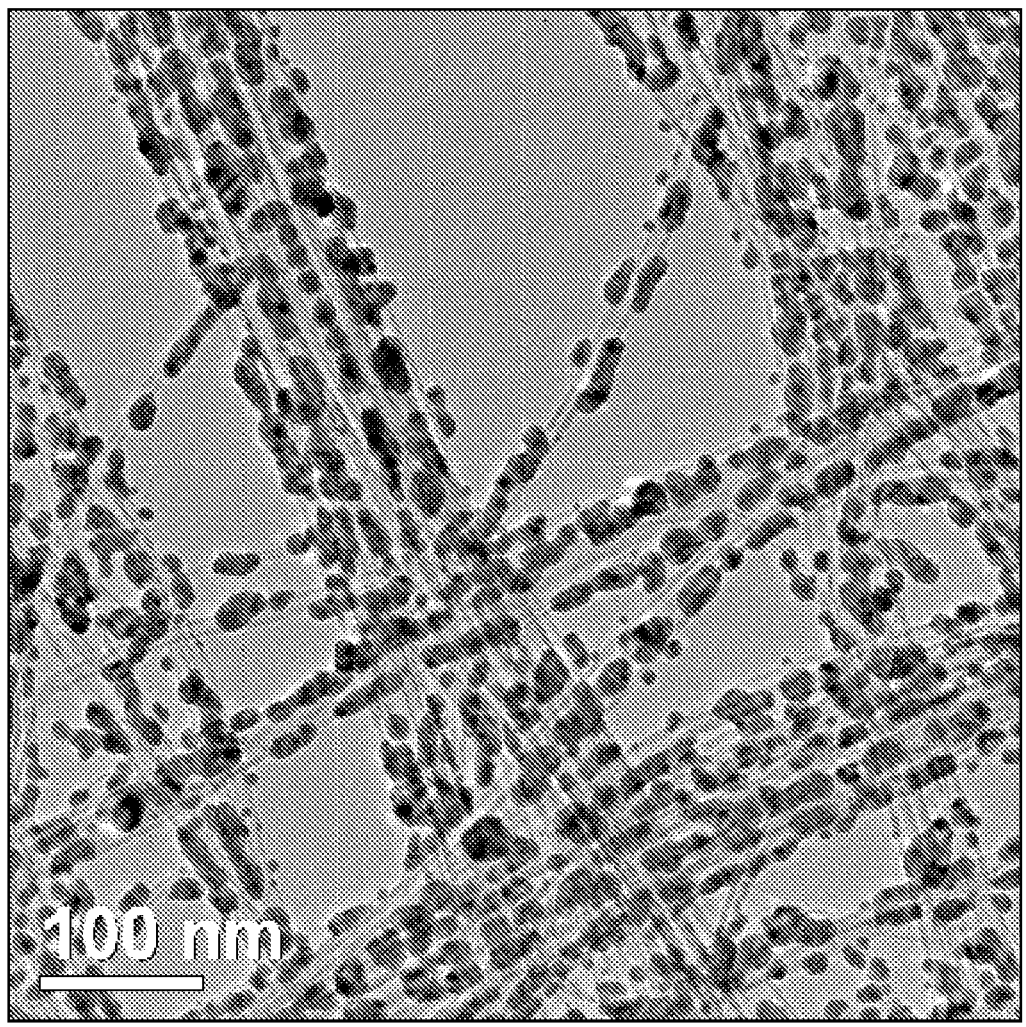
FIG. 5 shows a low magnification Transmission Electron Microscope (TEM) image of an SERS substrate defined as an Ag-CNT grid.
Figure 6:
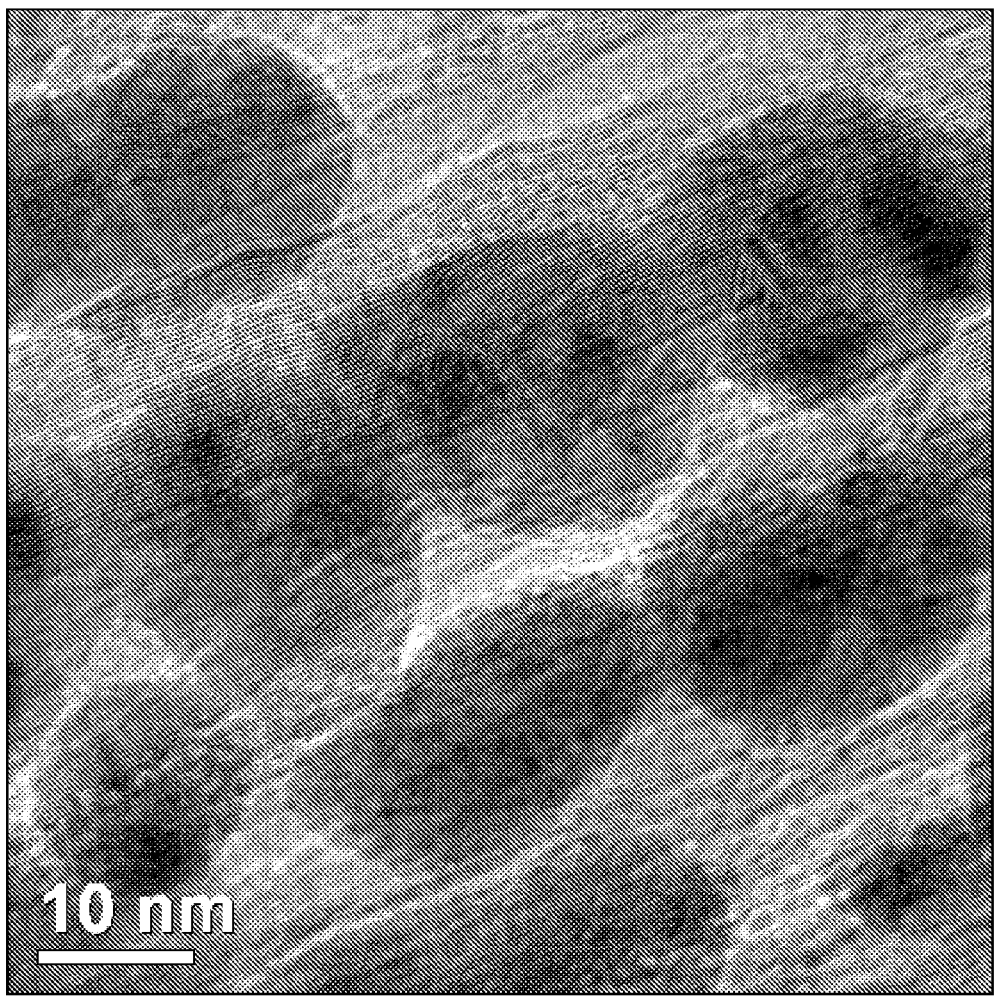
FIG. 6 shows a high magnification TEM image of the SERS substrate in FIG. 5.
Figure 7:
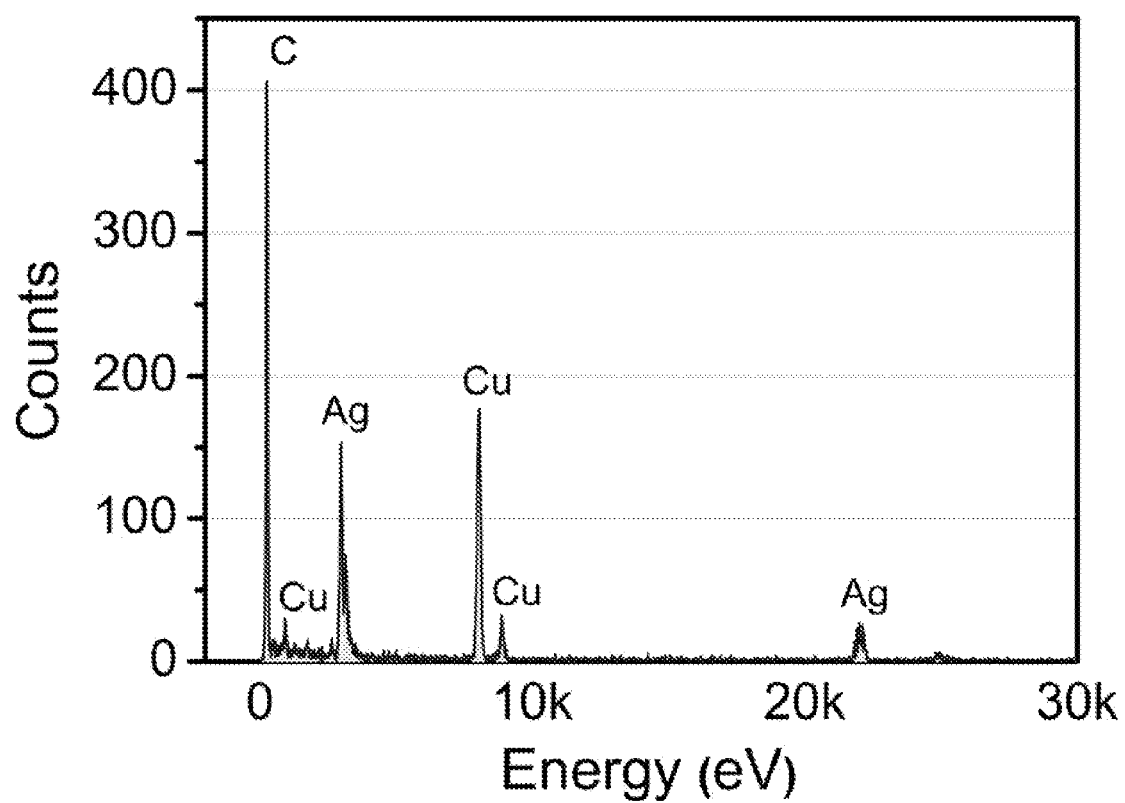
FIG. 7 shows an Energy Dispersive Spectrometer (EDS) image of the SERS substrate in FIG. 5.
Figure 8:
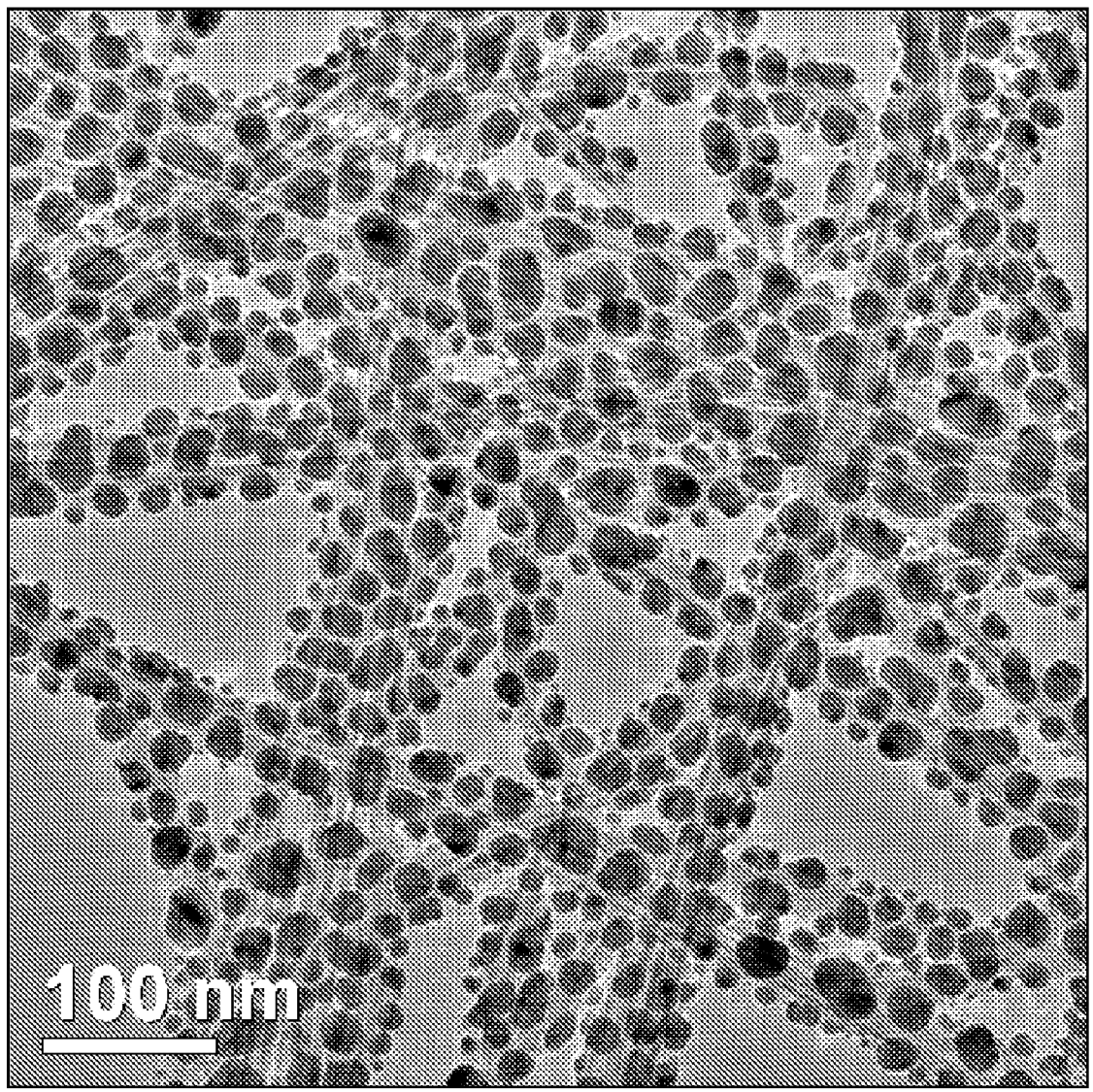
FIG. 8 shows a low magnification TEM image of an SERS substrate defined as an Ag—$SiO_2$-CNT grid.
Figure 9:
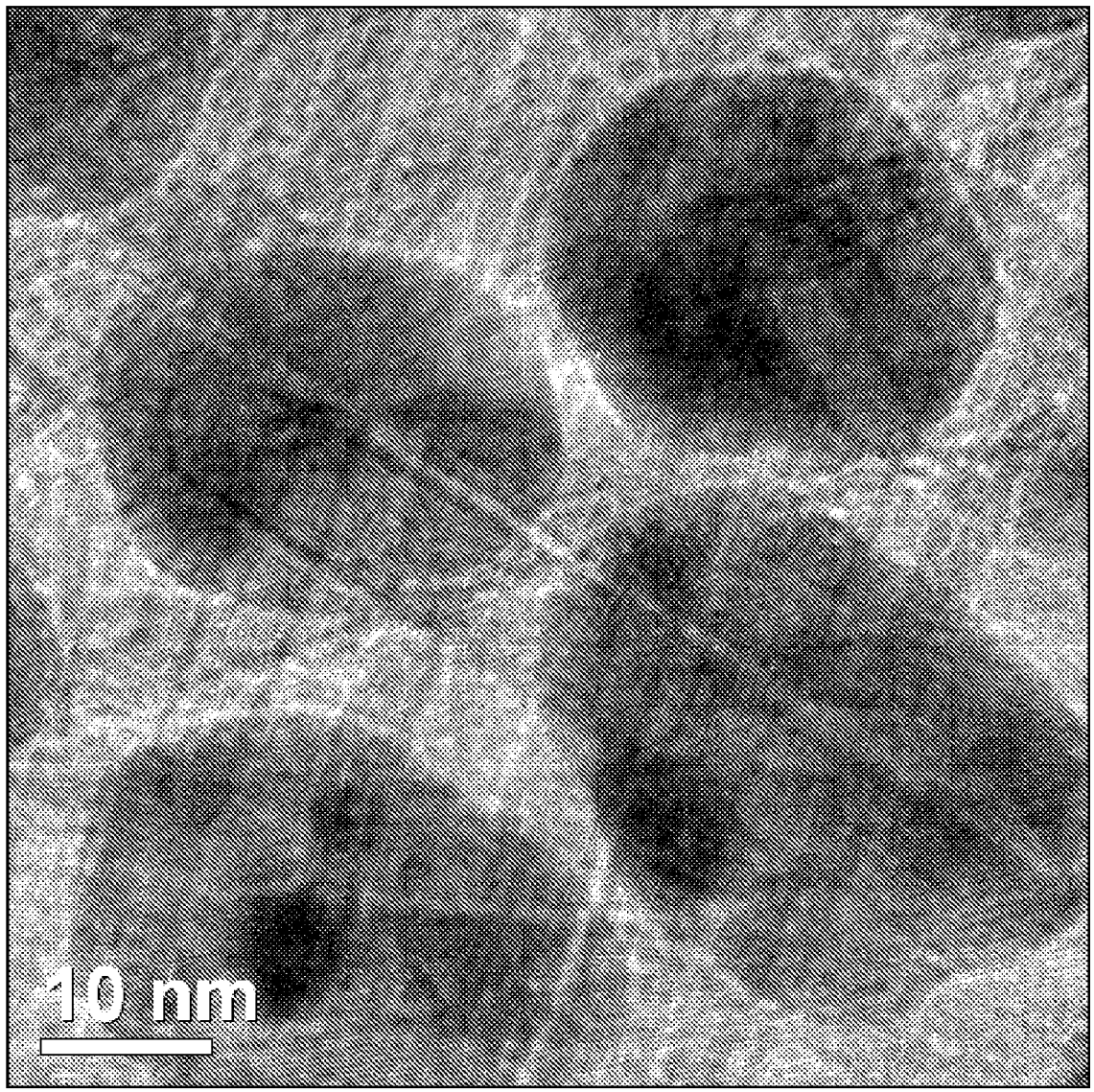
FIG. 9 shows a high magnification TEM image of the SERS substrate in FIG. 8.

The plurality of stacked carbon nanotube films as shown in FIG. 2 can be defined as a CNT grid. Referring to FIG. 5 and FIG. 6, a SERS substrate 120, 220 including the CNT grid and a silver film can be defined as an Ag-CNT grid. The silver film can be disposed on a surface of the CNT grid, and have a thickness of about 5 nanometers. An Energy Dispersive Spectrometer (EDS) image of the Ag-CNT grid is shown in FIG. 7. In FIG. 7, the copper is from a TEM micro gird, thus, the elements of the Ag-CNT grid can include of silver and carbon. Referring to FIG. 8 and FIG. 9, an SERS substrate 120, 220 including the CNT grid, a silicon dioxide layer, and a silver film can be provided and be named as an Ag—SiO$_2$-CNT grid. The silicon dioxide layer is deposited on the CNT grid, and the silver film is deposited on the silicon dioxide layer. The silver film can have a thickness of about 5 nanometers. The silicon dioxide layer can have a thickness of about 20 nanometers.

Figure 10:
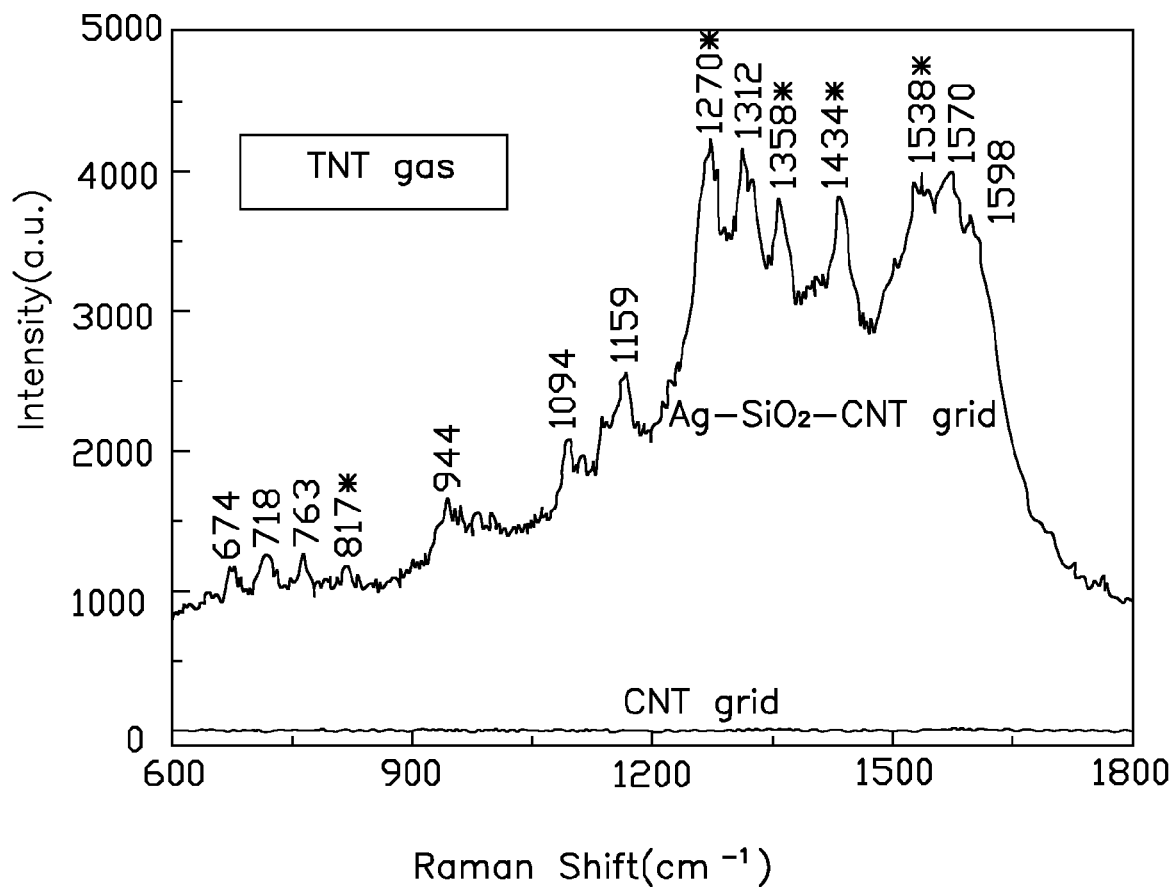
FIG. 10 shows a comparison of Raman spectra of TNT on the CNT grid and the Ag—$SiO_2$-CNT grid.

To test a Raman-enhancing capability of the Raman detecting system 100, 200, the SERS substrate 120, 220 were put above a TNT powder in a desiccator for several hours at about 25 before the Raman spectra is taken. The adsorbed TNT vapor can be detected on the Ag—SiO$_2$-CNT grid as shown in FIG. 10. Due to different adsorption geometry of TNT molecules on the SERS substrates 120, 220, the details of the Raman spectra for the TNT solution and vapor are different, but the peak at about 1430 cm$^{-1}$, the NO$_2$ symmetric stretching vibration mode near 1360 cm$^{-1}$, and the band near 1270 cm$^{-1}$, could be used as a "fingerprint" for the detection of TNT as aforementioned. This result indicates that the SERS substrates can be used for detecting ambient TNT vapor. For comparison, identical experiments were also performed using a conventional planar SERS substrate, and a pure CNT grid, respectively, but no signals could be detected on these substrates.

An detection method for detecting the explosive, includes steps of:
S10, providing a surface-enhanced Raman scattering (SERS) substrate to absorb a vapor of the explosive;
S20, illuminating the explosive on the SERS substrate; and
S30, detecting a Raman scattered light scattered from the explosive.

In step S10, the substrate includes a carbon nanotube film structure and a plurality of metallic particles disposed on the carbon nanotube film structure. The carbon nanotube film structure includes a plurality of stacked carbon nanotube films. Each of the carbon nanotube films includes a plurality of carbon nanotubes substantially parallel to a surface of the carbon nanotube film.

Finally, it is to be understood that the above-described embodiments are intended to illustrate rather than limit the disclosure. Variations may be made to the embodiments without departing from the spirit of the disclosure as claimed. Elements associated with any of the above embodiments are envisioned to be associated with any other embodiments. The above-described embodiments illustrate the scope of the disclosure but do not restrict the scope of the disclosure.

What is claimed is:

1. A Raman detecting system, comprising:
    a surface-enhanced Raman scattering substrate comprising a carbon nanotube film structure and a plurality of metallic particles disposed on the carbon nanotube film structure, the carbon nanotube film structure absorbing a vapor of an explosive;
    a projecting module projecting a beam of light to the substrate; and
    a receiving module collecting the light scattered by the substrate;
    wherein the carbon nanotube film structure comprises a plurality of stacked carbon nanotube films, each of the carbon nanotube films comprises a plurality of carbon nanotubes substantially parallel to a surface of the carbon nanotube film.

2. The system of claim 1, wherein the number of layers of the carbon nanotube films is less than or equal to 10.

3. The system of claim 1, wherein adjacent carbon nanotube films are adhered by van der Waals attractive forces therebetween.

4. The system of claim 1, wherein in each carbon nanotube film, the carbon nanotubes are substantially aligned in a single direction and joined end to end by van der Waals attractive forces therebetween.

5. The system of claim 1, wherein aligned directions of adjacent carbon nanotube films are substantially perpendicular to each other.

6. The system of claim 1, wherein the carbon nanotubes of the carbon nanotube film structure define a plurality of micropores.

7. The system of claim 6, wherein each of the micropores has a size of about 1 nanometer to about 500 nanometers.

8. The system of claim 1, further comprising a framing element, wherein a part of the carbon nanotube film structure is attached to the framing element, and another part of the carbon nanotube structure film is suspended.

9. The system of claim 1, wherein interparticle gaps are formed among the particles, each of the interparticle gaps is about 1 nanometer to about 15 nanometers.

10. The system of claim 9, wherein each of the interparticle gaps is about 2 nanometers to about 5 nanometers.

11. The system of claim 1, wherein each of the metallic particles has a diameter of about 1 nanometer to about 50 nanometers.

12. The system of claim 11, wherein the diameter of each of the metallic particles is about 18 nanometers to about 22 nanometers.

13. The system of claim 11, wherein the diameter of each of the metallic particles is about 3 nanometers to about 7 nanometers.

14. The system of claim 1, wherein the carbon nanotube film structure further comprises transition layers disposed between the carbon nanotube film structure and the metallic particles to provide a smooth surface for disposing the metallic particles.

15. The system of claim 14, wherein the transition layer has a thickness of about 1 nanometer to about 50 nanometers.

16. The system of claim 15, wherein the thickness of the transition layer is about 3 nanometers to about 7 nanometers.

17. A Raman detecting system, comprising
    a chamber receiving a sample to be detected therein;
    a surface-enhanced Raman scattering substrate absorbing a vapor of the sample, the substrate comprising a carbon nanotube film structure and a metallic layer disposed on the carbon nanotube film structure;
    a projecting module projecting a beam of light to the substrate; and
    a receiving module collecting the light scattered by the substrate;
    wherein the carbon nanotube film structure comprises a plurality of stacked carbon nanotube films, each of the carbon nanotube films comprises a plurality of carbon nanotubes, the carbon nanotubes form a plurality of micropores and nodes.

18. The system of claim 17, wherein the chamber is selected from the group consisting of a room, an airport, a container, a railway station, a carriage, and combinations thereof.

19. A detection method for detecting a explosive, comprising:
    providing a surface-enhanced Raman scattering substrate to absorb a vapor of the explosive;
    illuminating the explosive on the substrate; and
    detecting a Raman scattered light scattered from the explosive;
    wherein the substrate comprises a carbon nanotube film structure and a plurality of metallic particles disposed on the carbon nanotube film structure, the carbon nanotube film structure comprises a plurality of stacked carbon nanotube films, each of the carbon nanotube films comprises a plurality of carbon nanotubes substantially parallel to a surface of the carbon nanotube film.

* * * * *